(12) United States Patent
Commons et al.

(10) Patent No.: US 7,538,107 B2
(45) Date of Patent: May 26, 2009

(54) OXAZINAN-2-ONE DERIVATIVES USEFUL AS PR MODULATORS

(75) Inventors: Thomas Joseph Commons, Wayne, PA (US); Andrew Fensome, Wayne, PA (US); Gavin David Heffernan, Florence, NJ (US); Casey Cameron McComas, Phoenixville, PA (US); Richard Page Woodworth, Jr., North Wales, PA (US); Michael Byron Webb, Douglassville, PA (US); Michael Anthony Marella, Limerick, PA (US); Edward George Melenski, Collegeville, PA (US); Ronald Charles Bernotas, Royersford, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/891,821

(22) Filed: Aug. 13, 2007

(65) Prior Publication Data
US 2008/0045518 A1 Feb. 21, 2008

Related U.S. Application Data

(60) Provisional application No. 60/837,820, filed on Aug. 15, 2006.

(51) Int. Cl.
C07D 413/04 (2006.01)
A61K 31/5355 (2006.01)

(52) U.S. Cl. .................................... 514/228.8; 544/96
(58) Field of Classification Search .................... 544/96; 514/228.8
See application file for complete search history.

(56) References Cited

U.S. PATENT DOCUMENTS

| | | | |
|---|---|---|---|
| 4,008,243 A | 2/1977 | Wikel et al. | |
| 4,150,028 A | 4/1979 | Paget et al. | |
| 4,216,313 A | 8/1980 | Paget et al. | |
| 4,268,679 A | 5/1981 | Lavanish | |
| 4,293,558 A | 10/1981 | Paget et al. | |
| 4,426,527 A | 1/1984 | Lavanish et al. | |
| 4,756,744 A | 7/1988 | Schwindemann | |
| 5,719,136 A | 2/1998 | Chwalisz et al. | |
| 5,972,372 A | 10/1999 | Saleh et al. | |
| 6,125,850 A | 10/2000 | Sokal et al. | |
| 6,126,958 A | 10/2000 | Saleh et al. | |
| 6,531,470 B1 | 3/2003 | Gordeev et al. | |
| 2002/0115669 A1 | 8/2002 | Wiedeman et al. | |
| 2002/0183371 A1 | 12/2002 | Gordeev et al. | |
| 2003/0114491 A1 | 6/2003 | Kim et al. | |
| 2004/0157883 A1 | 8/2004 | Chen et al. | |
| 2004/0167192 A1 | 8/2004 | Solow-Cordero et al. | |
| 2004/0214870 A1 | 10/2004 | Xin et al. | |

FOREIGN PATENT DOCUMENTS

DE 32 27 329 A1 1/1984
DE 196 01 264 A1 7/1997
DE 196 04 223 A1 8/1997
DE 196 49 095 A1 8/1997
DE 100 34 622 A1 1/2002
DE 100 34 623 A1 1/2002
DE 100 34 628 A1 1/2002
EP 0 300 272 B1 9/1992
EP 0 244 803 B1 10/1994
EP 0 770 613 B1 10/1996
EP 0 894 497 B1 7/1998
FR 1514028 1/1968
GB 1127875 9/1968
JP 7-149745 6/1995
JP 9/216885 8/1997
NL 6703864 3/1967
NL 6706448 5/1967
WO WO 92/07567 A1 5/1992
WO WO 92/09586 A1 6/1992
WO WO 95/15955 A1 6/1995
WO WO 97/36882 A1 10/1997
WO WO 98/00420 A1 1/1998
WO WO 98/04534 A1 2/1998
WO WO 99/64416 A2 12/1999
WO WO 99/64417 A2 12/1999
WO WO 00/01676 A1 1/2000
WO WO 01/70733 A2 9/2001
WO WO 02/50071 A1 6/2002
WO WO 02/081453 A1 10/2002
WO WO 03/011859 A2 2/2003
WO WO 03/027085 A2 4/2003

(Continued)

OTHER PUBLICATIONS

Wolff Manfred E. "Burger's Medicinal Chemistry, 5ed, Part 1", John Wiley & Sons, 1995, pp. 975-977.*

(Continued)

*Primary Examiner*—Kahsay T Habte
(74) *Attorney, Agent, or Firm*—Stephen E. Johnson

(57) ABSTRACT

Compounds of the following structure are described:

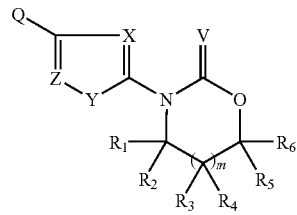

wherein $R_1$-$R_6$, m, V, X, Y, Z and Q are described herein, or a pharmaceutically acceptable salt, tautomer, metabolite or prodrug thereof. These compounds are useful for treating a variety of hormone-related conditions including contraception, treating or preventing fibroids, endometriosis, dysfunctional bleeding, uterine leiomyomata, polycystic ovary syndrome, or hormone-dependent carcinomas, providing hormone replacement therapy, stimulating food intake or synchronizing estrus.

22 Claims, No Drawings

FOREIGN PATENT DOCUMENTS

| WO | WO 03/101985 A1 | 12/2003 |
|---|---|---|
| WO | WO 2004/014384 A2 | 2/2004 |
| WO | WO 2004/014899 A1 | 2/2004 |
| WO | WO 2004/019938 A1 | 3/2004 |
| WO | WO 2004/087698 A2 | 10/2004 |
| WO | WO 2004/089303 A2 | 10/2004 |
| WO | WO 2005/005435 A1 | 1/2005 |

OTHER PUBLICATIONS

Banker, G.S. et al, "Modern Pharmaceutics, 3ed.", Marcel Dekker, New York. 1996, pp. 451 and 596.*

U.S. Appl. No. 11/891,729, filed Aug. 13, 2007, Commons et al.
U.S. Appl. No. 11/891,727, filed Aug. 13, 2007, Commons et al.
U.S. Appl. No. 11/891,747, filed Aug. 13, 2007, Commons et al.
U.S. Appl. No. 11/891,728, filed Aug. 13, 2007, Commons et al.
U.S. Appl. No. 11/891,748, filed Aug. 13, 2007, Commons et al.

David J. Mangelsdorf, Carl Thummel, Miguel Beato, Peter Herrlich, Günther Schütz, Kazuhiko Umesono, Bruce Blumberg, Philippe Kastner, Manuel Mark, Pierre Chambon and Ronald M. Evans, The nuclear receptor superfamily: The second decade, Cell, vol. 83, Issue 6, Dec. 15, 1995, pp. 835-839.

AndréUlmann, Rémi Peyron and Louise Silvestre, Clinical Uses of Mifepristone (MFP), Annals of the New York Academy of Sciences, Jun. 1995—vol. 761 Steroid Receptors and Antihormones, pp. 248-260.

Kekkonen, et al, Fertility and Sterility, 60, 610, 1993.

Horwitz, et al, Horm. Cancer, 283, 1996, pub: Birkhaeuser, Boston, Mass., ed. Vedeckis.

AA Murphy, LM Kettel, AJ Morales, VJ Roberts, and SS Yen, Regression of uterine leiomyomata in response to the antiprogesterone RU 486, J Clin Endocrinol Metab 1993 76: 513-517.

Kettel, et al., Fertility and Sterility, 56, 402, 1991.

Horst Michna, Karsten Parczyk, Martin R. Schneider and Yukishige Nishino, Differentiation Therapy with Progesterone Antagonists Annals of the New York Academy of Sciences, Jun. 1995—vol. 761 Steroid Receptors and Antihormones, pp. 224-247.

B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

* cited by examiner

OXAZINAN-2-ONE DERIVATIVES USEFUL AS PR MODULATORS

CROSS-REFERENCE TO RELATED APPLICATIONS

This application claims the benefit of the priority of U.S. Provisional Patent Application No. 60/837,820, filed Aug. 15, 2006.

BACKGROUND OF THE INVENTION

This invention relates to modulators of the progesterone receptor, their preparation and utility.

Intracellular receptors (IR) form a class of structurally related gene regulators known as "ligand dependent transcription factors" (Mangelsdorf, D. J. etc. Cell, 83, 835, 1995). The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as PR ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA, the complex modulates the production of mRNA and the protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, either alone or in the presence of an ER agonist.

PR antagonists may also be used in contraception (Ulmann, et al., Ann. N.Y. Acad. Sci., 261, 248, 1995; Kekkonen, et al, Fertility and Sterility, 60, 610, 1993; or U.S. Pat. No. 5,719,136); for the treatment of hormone dependent breast cancers (Horwitz, et al, Horm. Cancer, 283, 1996, pub: Birkhaeuser, Boston, Mass., ed. Vedeckis), uterine and ovarian cancers, non-malignant chronic conditions such as uterine fibroids (Murphy, et al, J. Clin. Endo. Metab., 76, 513, 1993) and endometriosis (Kettel, et al., Fertility and Sterility, 56, 402, 1991), hormone dependent prostate cancer (Michna, et al, Ann. N.Y. Acad. Sci., 761, 224, 1995); and for hormone replacement therapy (U.S. Pat. No. 5,719,136).

What is needed in the art are alternative progesterone receptor modulators.

SUMMARY OF THE INVENTION

In one aspect, progesterone receptor modulators of the following structure are provided, wherein $R_1$-$R_6$, m, V, X, Y, Z, and Q are defined herein:

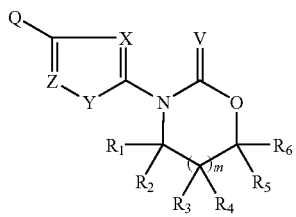

In a further aspect, compounds of the following structure are provided, wherein $R_1$-$R_6$, $R_{15}$, m, q, V, X, and Y are defined herein:

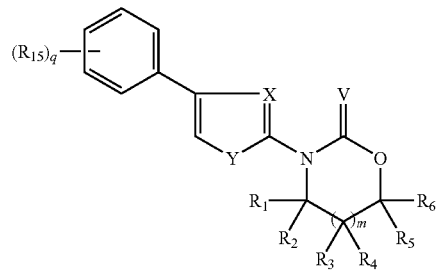

In yet another aspect, compounds of the following structure are provided, wherein $R_1$-$R_6$, $R_{15}$, m, q, D, V, X, and Y are defined herein:

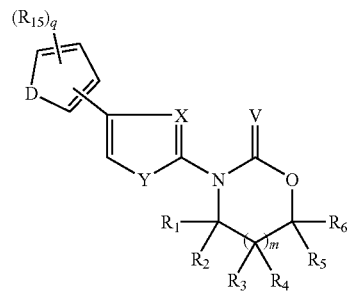

In still a further aspect, methods of contraception using the compounds described herein are provided.

In yet another aspect, methods of treating or preventing fibroids using the compounds described herein are provided.

In a further aspect, methods for treating or preventing endometriosis, dysfunctional bleeding, uterine leiomyomata, polycystic ovary syndrome, or hormone-dependent carcinomas using the compounds described herein are provided.

In still a further aspect, methods of providing hormone replacement therapy using the compounds described herein are provided.

In another aspect, methods of stimulating food intake or synchronizing estrus using the compounds described herein are provided.

Other aspects and advantages of the invention will be readily apparent from the following detailed description of the invention.

DETAILED DESCRIPTION OF THE INVENTION

Novel compounds, which are useful as progesterone receptor modulators, are described. These compounds are useful in treating and/or preventing a variety of hormone-related conditions as described below.

I. The Compounds

The compounds described herein have the following general structure:

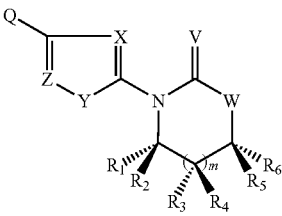

wherein, $R_1$, $R_2$, $R_3$, $R_4$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_nC(H)_{3-p}(R_7)_p$, —$(CH_2)_nCOOR_8$, or —$(CH_2)_p$—O—$R_9$; or $R_1$, $R_2$ or $R_3$, $R_4$ or $R_5$, $R_6$ are taken together to form a carbon-based 3 to 6 membered saturated ring; or when m is 0, $R_1$ or $R_2$ forms a carbon-based 5 to 7 membered saturated ring with $R_5$ or $R_6$; or $R_1$ or $R_2$ form a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; W is O, $NR_{10}$ or $CR_{11}R_{12}$; $R_{10}$ is H, $C_1$ to $C_6$ alkyl, or $(CH_2)_n$-aryl; $R_{11}$ and $R_{12}$ are, independently, H, $C_1$ to $C_6$ alkyl, or —$(CH_2)_n$-aryl; or $R_{11}$ or $R_{12}$ forms a double bond with $R_5$ or $R_6$; V is O, S or $NR_{13}$; or when m is 0, W is O, $R_1$ and $R_2$ are H or are taken together with oxygen to form a carbonyl group, V is —$(CH_3)_2$; or when m is 1, V is O and W is $CR_{11}R_{12}$ then $R_1$ or $R_2$ can form a two carbon bridge with $R_{11}$ or $R_{12}$; $R_{13}$ is H, $C_1$ to $C_6$ alkyl, $(CH_2)_n$-aryl, $(CH_2)_n$—CN, CO—($C_1$ to $C_6$ alkyl), CO—$(CH_2)_n$-aryl, $SO_2$—($C_1$ to $C_6$ alkyl), or $SO_2$—$(CH_2)_n$-aryl; X and Z are, independently, N or $CR_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy or $(CH_2)_n$—CN; or when Z is $CR_{14}$, $R_{14}$ forms a two carbon saturated or unsaturated bond with Q to provide a tricyclic ring system; Y is S; or Y is O when X is N and Z is $CR_{14}$; Q is aryl, substituted aryl, heteroaryl, or substituted heteroaryl; m is 0 or 1; n is 0 to 3; and p is 1 to 3, or a pharmaceutically acceptable salt, tautomer, metabolite or prodrug thereof.

In one embodiment, the compounds are of the structure:

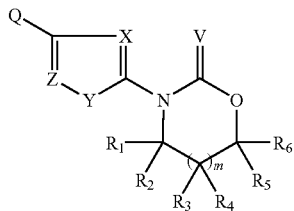

wherein, $R_1$, $R_2$, $R_3$, $R_4$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_nC(H)_{3-p}(R_7)_p$, —$(CH_2)_nCOOR_8$, or —$(CH_2)_p$—O—$R_9$; or $R_1$, $R_2$ or $R_3$, $R_4$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; V is O or S; X and Z are, independently, N or $CR_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN; Y is O or S; Q is aryl, substituted aryl, heteroaryl, or substituted heteroaryl; m is 1; n is 0 to 3; p is 1 to 3; or a pharmaceutically acceptable salt, tautomer, metabolite or prodrug thereof.

V is suitably O. $R_1$ and $R_2$ are suitably each $C_1$ to $C_{10}$ alkyl. $R_5$ and $R_6$ are suitably each H. X is suitably N. Y is suitably S. Z is suitably $CR_{14}$.

In a further embodiment, V is O; $R_1$ and $R_2$ are $C_1$ to $C_{10}$ alkyl; and $R_5$ and $R_6$ are H.

In another embodiment, X is N; Y is S; and Z is $CR_{14}$.

In still a further embodiment, X and Z are N and Y is S.

In yet another embodiment, X is N; Y is O; and Z is $CR_{14}$.

In another embodiment, V is O; $R_1$ and $R_2$ are $C_1$ to $C_{10}$ alkyl; $R_5$ and $R_6$ are H; X is N; Y is S; and Z is $CR_{14}$.

In yet a further embodiment, Q is aryl is substituted aryl.

In a further embodiment, Q is an aromatic carbon-based ring, such as an optionally substituted benzene ring. The optionally substituted benzene ring may be substituted by one or more of $R_{15}$ and $R_{15}$ is $(CH_2)_nCN$, halogen, $NO_2$, —$C(NH_2)$=NOH, $C_1$ to $C_3$ perfluoroalkyl, $C_1$ to $C_3$ perfluoroalkoxy, —O($C_1$ to $C_4$ alkyl), —O($C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl. Desirably, $R_{15}$ is CN, halogen, or $NO_2$.

The compound described herein therefore can be of the following structure, wherein the $R_{15}$ group is bound to one or more of the carbon-atoms of the benzene ring:

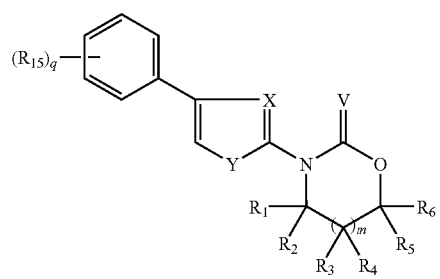

wherein, $R_1$-$R_6$, m, V, X, and Y are defined herein, $R_{15}$ is $(CH_2)_nCN$, halogen, $NO_2$, —$C(NH_2)$=NOH, $C_1$ to $C_3$ perfluoroalkyl, $C_1$ to $C_3$ perfluoroalkoxy, —O($C_1$ to $C_4$ alkyl), —O($C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl; and q is 1 to 4; or a pharmaceutically acceptable salt, tautomer, metabolite or prodrug thereof. Desirably, $R_1$, $R_2$, $R_5$, and $R_6$, are, independently, H or $C_1$ to $C_{10}$ alkyl.

The compound may also be of the structure:

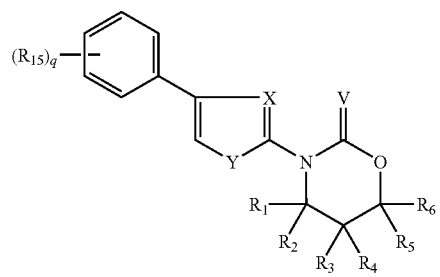

wherein, $R_1$-$R_6$, V, X, and Y are defined herein, $R_{15}$ is $(CH_2)_n$CN, halogen, $NO_2$, —$C(NH_2)$=NOH, $C_1$ to $C_3$ perfluoroalkyl, $C_1$ to $C_3$ perfluoroalkoxy, —O($C_1$ to $C_4$ alkyl), —O($C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—(CH$_2$)$_2$-aryl, —COO—(C$_1$ to C$_4$ alkyl), —COO—(C$_1$ to C$_4$ substituted alkyl), —CONH—(C$_1$ to C$_3$ alkyl), —CON—(C$_1$ to C$_3$ alkyl)$_2$, aryl, substituted aryl, heteroaryl, or substituted heteroaryl; and q is 1 to 4; or a pharmaceutically acceptable salt, tautomer, metabolite or prodrug thereof. Desirably, R$_1$, R$_2$, R$_5$, and R$_6$ are, independently, H or C$_1$ to C$_{10}$ alkyl.

In yet another embodiment, Q is heteroaryl or substituted heteroaryl. In one example, the heteroaryl ring is substituted by one or more R$_{15}$, wherein R$_{15}$ is (CH$_2$)$_n$CN, halogen, NO$_2$, —C(NH$_2$)=NOH, C$_1$ to C$_3$ perfluoroalkyl, C$_1$ to C$_3$ perfluoroalkoxy, —O(C$_1$ to C$_4$ alkyl), —O(C$_1$ to C$_4$ substituted alkyl), —SO$_2$—(C$_1$ to C$_4$ alkyl), —SO$_2$—(C$_1$ to C$_4$ substituted alkyl), —CO—(C$_1$ to C$_4$ alkyl), —CO—(C$_1$ to C$_4$ substituted alkyl), C$_1$ to C$_4$ alkyl, C$_1$ to C$_4$ substituted alkyl, —O—(CH$_2$)$_n$-aryl, —COO—(C$_1$ to C$_4$ alkyl), —COO—(C$_1$ to C$_4$ substituted alkyl), —CONH—(C$_1$ to C$_3$ alkyl), —CON—(C$_1$ to C$_3$ alkyl)$_2$, aryl, substituted aryl, heteroaryl, or substituted heteroaryl.

The compound described herein may, therefore, be of the structure, wherein the R$_{15}$ group is bound to one or more of the carbon-atoms of the heterocyclic group:

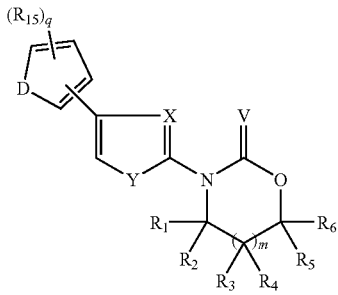

wherein, R$_1$-R$_6$, m, V, X, and Y are defined herein, D is S, NR$_{16}$, or O; R$_{15}$ is (CH$_2$)$_n$CN, halogen, NO$_2$, —C(NH$_2$)=NOH, C$_1$ to C$_3$ perfluoroalkyl, C$_1$ to C$_3$ perfluoroalkoxy, —O(C$_1$ to C$_4$ alkyl), —O(C$_1$ to C$_4$ substituted alkyl), —SO$_2$—(C$_1$ to C$_4$ alkyl), —SO$_2$—(C$_1$ to C$_4$ substituted alkyl), —CO—(C$_1$ to C$_4$ alkyl), —CO—(C$_1$ to C$_4$ substituted alkyl), C$_1$ to C$_4$ alkyl, C$_1$ to C$_4$ substituted alkyl, —O—(CH$_2$)$_n$-aryl, —COO—(C$_1$ to C$_4$ alkyl), —COO—(C$_1$ to C$_4$ substituted alkyl), —CONH—(C$_1$ to C$_3$ alkyl), —CON—(C$_1$ to C$_3$ alkyl)$_2$, aryl, substituted aryl, heteroaryl, or substituted heteroaryl; R$_{16}$ is H, C$_1$ to C$_6$ alkyl, C$_1$ to C$_6$ substituted alkyl, or —COO—(C$_1$ to C$_6$ alkyl); and q is 1 to 3; or a pharmaceutically acceptable salt, tautomer, metabolite or prodrug thereof. Desirably, R$_1$, R$_2$, R$_5$, and R$_6$ are, independently, H or C$_1$ to C$_{10}$ alkyl.

In another example, the compound is of the structure:

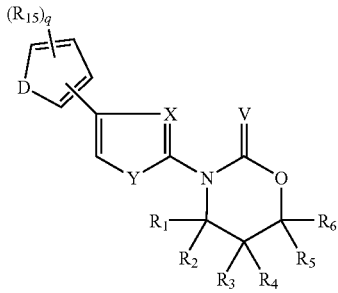

wherein, R$_1$-R$_6$, V, X, and Y are defined herein, D is S, NR$_{16}$, or O; R$_{15}$ is (CH$_2$)$_n$CN, halogen, NO$_2$, —C(NH$_2$)=NOH, C$_1$ to C$_3$ perfluoroalkyl, C$_1$ to C$_3$ perfluoroalkoxy, —O(C$_1$ to C$_4$ alkyl), —O(C$_1$ to C$_4$ substituted alkyl), —SO$_2$—(C$_1$ to C$_4$ alkyl), —SO$_2$—(C$_1$ to C$_4$ substituted alkyl), —CO—(C$_1$ to C$_4$ alkyl), —CO—(C$_1$ to C$_4$ substituted alkyl), C$_1$ to C$_4$ alkyl, C$_1$ to C$_4$ substituted alkyl, —O—(CH$_2$)$_n$-aryl, —COO—(C$_1$ to C$_4$ alkyl), —COO—(C$_1$ to C$_4$ substituted alkyl), —CONH—(C$_1$ to C$_3$ alkyl), —CON—(C$_1$ to C$_3$ alkyl)$_2$, aryl, substituted aryl, heteroaryl, or substituted heteroaryl; R$_{16}$ is H, C$_1$ to C$_6$ alkyl, C$_1$ to C$_6$ substituted alkyl, or —COO—(C$_1$ to C$_6$ alkyl); and q is 1 to 3; or a pharmaceutically acceptable salt, tautomer, metabolite or prodrug thereof. Desirably, R$_1$, R$_2$, R$_5$, and R$_6$ are, independently, H or C$_1$ to C$_{10}$ alkyl.

In still a further embodiment, the compound is of the structure:

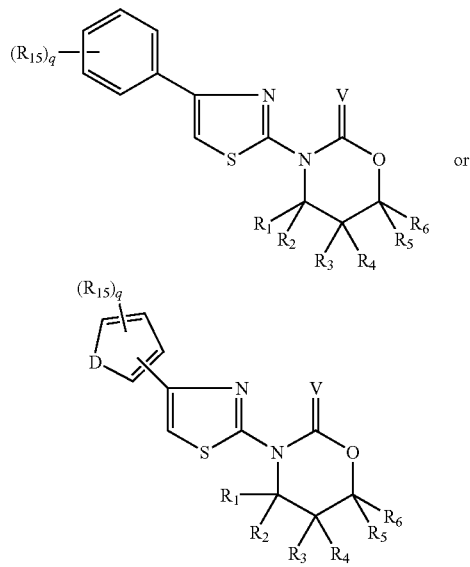

wherein, R$_1$, R$_2$, R$_3$, R$_4$, R$_5$ and R$_6$ are, independently, H, C$_1$ to C$_{10}$ alkyl, —(CH$_2$)$_n$-aryl, —(CH$_2$)$_p$—O—(CH$_2$)$_n$-aryl, —(CH$_2$)$_n$C(H)$_{3-p}$(R$_7$)$_p$, —(CH$_2$)$_n$COOR$_8$, or —(CH$_2$)$_p$—O—R$_9$; or R$_1$, R$_2$, or R$_3$, or R$_4$, or R$_5$, R$_6$ are taken together to form a carbon-based 3 to 6 membered saturated ring; R$_7$ is halogen; R$_8$ is C$_1$ to C$_6$ alkyl; R$_9$ is H, C$_1$ to C$_6$ alkyl, or C$_1$ to C$_3$ perfluoroalkyl; D is S, NR$_{16}$, or O; R$_{15}$ is (CH$_2$)$_n$CN, halogen, NO$_2$, —C(NH$_2$)=NOH, C$_1$ to C$_3$ perfluoroalkyl, C$_1$ to C$_3$ perfluoroalkoxy, —O(C$_1$ to C$_4$ alkyl), —SO$_2$—(C$_1$ to C$_4$ alkyl), —CO—(C$_1$ to C$_4$ alkyl), C$_1$ to C$_4$ alkyl, —O—(CH$_2$)$_n$-aryl, —COO—(C$_1$ to C$_4$ alkyl), —CONH—(C$_1$ to C$_3$ alkyl), —CON—(C$_1$ to C$_3$ alkyl)$_2$, aryl, or heteroaryl; R$_{16}$ is H, C$_1$ to C$_6$ alkyl, C$_1$ to C$_6$ substituted alkyl, or —COO—(C$_1$ to C$_6$ alkyl); V is O or S; n is 0 to 3; p is 1 to 3; q is 1 to 3; or a pharmaceutically acceptable salt, tautomer, metabolite, or prodrug thereof.

In yet another embodiment, the compound is of the structure:

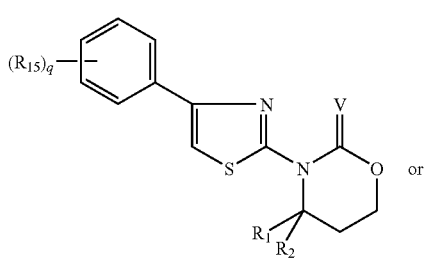

-continued

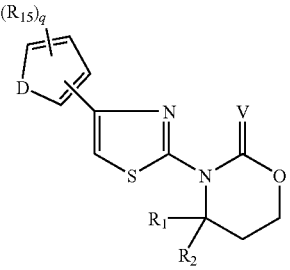

wherein, $R_1$ and $R_2$ are, independently, H, $C_1$ to $C_{10}$ alkyl, $-(CH_2)_n$-aryl, $-(CH_2)_p-O-(CH_2)_n$-aryl, $-(CH_2)_nC(H)_{3-p}(R_7)_p$, $-(CH_2)_nCOOR_8$, or $-(CH_2)_p-O-R_9$; or $R_1$ and $R_2$ are taken together to form a carbon-based 3 to 6 membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is $(CH_2)_nCN$, halogen, $NO_2$, $-C(NH_2)=NOH$, $C_1$ to $C_3$ perfluoroalkyl, $C_1$ to $C_3$ perfluoroalkoxy, $-O(C_1$ to $C_4$ alkyl), $-SO_2-(C_1$ to $C_4$ alkyl), $-CO-(C_1$ to $C_4$ alkyl), $C_1$ to $C_4$ alkyl, $-O-(CH_2)_n$-aryl, $-COO-(C_1$ to $C_4$ alkyl), $-CONH-(C_1$ to $C_3$ alkyl), $-CON-(C_1$ to $C_3$ alkyl)$_2$, aryl, or heteroaryl; $R_{16}$ is H, $C_1$ to $C_6$ alkyl, $C_1$ to $C_6$ substituted alkyl, or $-COO-(C_1$ to $C_6$ alkyl); V is O or S; n is 0 to 3; p is 1 to 3; q is 1 to 3; or a pharmaceutically acceptable salt, tautomer, metabolite, or prodrug thereof. Desirably, $R_1$ and $R_2$ are, independently, H or $C_1$ to $C_{10}$ alkyl.

In yet another embodiment, the compound is of the structure:

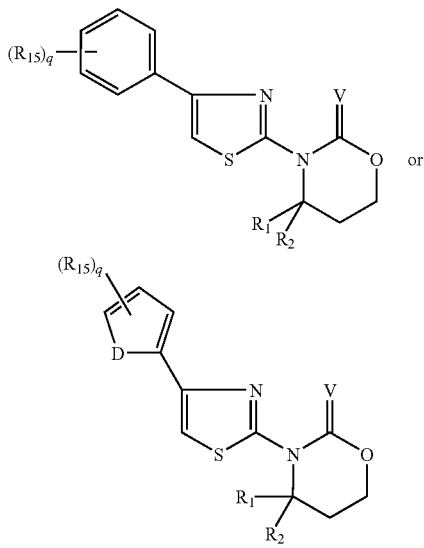

wherein, $R_1$ and $R_2$ are, independently, H, $C_1$ to $C_{10}$ alkyl, $-(CH_2)_n$-aryl, $-(CH_2)_p-O-(CH_2)$-aryl, $-(CH_2)_nC(H)_{3-p}(R_7)_p$, $-(CH_2)_nCOOR_8$, or $-(CH_2)_p-O-R_9$; or $R_1$ and $R_2$ are taken together to form a carbon-based 3 to 6 membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is $(CH_2)_nCN$, halogen, $NO_2$, $-C(NH_2)=NOH$, $C_1$ to $C_3$ perfluoroalkyl, $C_1$ to $C_3$ perfluoroalkoxy, $-O(C_1$ to $C_4$ alkyl), $-SO_2-(C_1$ to $C_4$ alkyl), $-CO-(C_1$ to $C_4$ alkyl), $C_1$ to $C_4$ alkyl, $-O-(CH_2)_n$-aryl, $-COO-(C_1$ to $C_4$ alkyl), $-CONH-(C_1$ to $C_3$ alkyl), $-CON-(C_1$ to $C_3$ alkyl)$_2$, aryl, or heteroaryl; $R_{16}$ is H, $C_1$ to $C_6$ alkyl, $C_1$ to $C_6$ substituted alkyl, or $-COO-(C_1$ to $C_6$ alkyl); V is O or S; n is 0 to 3; p is 1 to 3; q is 1 to 3; or a pharmaceutically acceptable salt, tautomer, metabolite, or prodrug thereof. Desirably, $R_1$ and $R_2$ are, independently, H or $C_1$ to $C_{10}$ alkyl.

In yet another embodiment, the compound is of the structure:

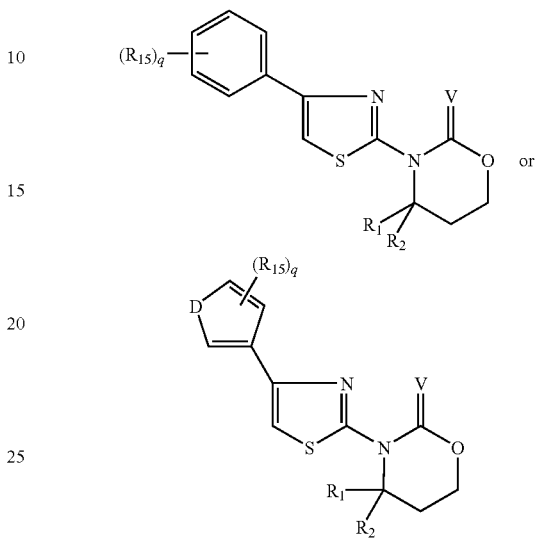

wherein, $R_1$ and $R_2$ are, independently, H, $C_1$ to $C_{10}$ alkyl, $-(CH_2)_n$-aryl, $-(CH_2)_p-O-(CH_2)_n$-aryl, $-(CH_2)_nC(H)_{3-p}(R_7)_p$, $-(CH_2)_nCOOR_8$, or $-(CH_2)_p-O-R_9$; or $R_1$ and $R_2$ are taken together to form a carbon-based 3 to 6 membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is $(CH_2)_nCN$, halogen, $NO_2$, $-C(NH_2)=NOH$, $C_1$ to $C_3$ perfluoroalkyl, $C_1$ to $C_3$ perfluoroalkoxy, $-O(C_1$ to $C_4$ alkyl), $-SO_2-(C_1$ to $C_4$ alkyl), $-CO-(C_1$ to $C_4$ alkyl), $C_1$ to $C_4$ alkyl, $-O-(CH_2)_n$-aryl, $-COO-(C_1$ to $C_4$ alkyl), $-CONH-(C_1$ to $C_3$ alkyl), $-CON-(C_1$ to $C_3$ alkyl)$_2$, aryl, or heteroaryl; $R_{16}$ is H, $C_1$ to $C_6$ alkyl, $C_1$ to $C_6$ substituted alkyl, or $-COO-(C_1$ to $C_6$ alkyl); V is O or S; n is 0 to 3; p is 1 to 3; q is 1 to 3; or a pharmaceutically acceptable salt, tautomer, metabolite, or prodrug thereof. Desirably, $R_1$ and $R_2$ are, independently, H or $C_1$ to $C_{10}$ alkyl.

The compound described herein may be selected from among 3-[4-(4-Bromophenyl)-1,3-thiazol-2-yl]-1,3-oxazinan-2-one and 3-[4-(4-Bromophenyl)-1,3-thiazol-2-yl]-5,5-dimethyl-1,3-oxazinan-2-one, or a pharmaceutically acceptable salt, tautomer, metabolite or prodrug thereof.

The compounds as described can contain one or more asymmetric centers and can thus give rise to optical isomers and diastereomers. The compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to 8 carbon atoms (i.e., $C_1$, $C_2$, $C_3$, $C_4$, $C_5$ $C_6$, $C_7$, or $C_8$). In another embodiment, an alkyl group has 1 to 6 carbon atoms (i.e., $C_1$, $C_2$, $C_3$, $C_4$, $C_5$ or $C_6$). In a further embodiment, an alkyl group has 1 to 4 carbon atoms (i.e., $C_1$, $C_2$, $C_3$, or $C_4$). Examples include methyl, ethyl, n-propyl, i-propyl, n-butyl, s-butyl, t-butyl, pentyl and hexyl, among others.

The term "cycloalkyl" is used herein to refer to cyclic, saturated aliphatic hydrocarbon groups. In one embodiment, a cycloalkyl group has 3 to 8 carbon atoms (i.e., $C_3$, $C_4$, $C_5$, $C_6$, $C_7$, or $C_8$). In another embodiment, a cycloalkyl group has 3 to 6 carbon atoms (i.e., $C_3$, $C_4$, $C_5$ or $C_6$). Examples include cyclopropyl, cyclobutyl, cyclopentyl and cyclohexyl, among others.

The term "alkenyl" is used herein to refer to both straight- and branched-chain alkyl groups having one or more carbon-carbon double bonds. In one embodiment, an alkenyl group contains 3 to 8 carbon atoms (i.e., $C_3$, $C_4$, $C_5$, $C_6$, $C_7$, or $C_8$). In another embodiment, an alkenyl group has 1 or 2 carbon-carbon double bonds and 3 to 6 carbon atoms (i.e., $C_3$, $C_4$, $C_5$ or $C_6$). Examples include propenyl, among others.

The term "alkynyl" is used herein to refer to both straight- and branched-chain alkyl groups having one or more carbon-carbon triple bonds. In one embodiment, an alkynyl group has 3 to 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to 6 carbon atoms (i.e., $C_3$, $C_4$, $C_5$, or $C_6$). Examples include propynyl, among others.

The terms "substituted alkyl", "substituted alkenyl", "substituted alkynyl", and "substituted cycloalkyl" refer to alkyl, alkenyl, alkynyl, and cycloalkyl groups, respectively, having one or more substituents e.g. 1 to 3 substituents which may be the same or different, selected from hydrogen, halogen, CN, OH, $NO_2$, amino, aryl, heterocyclyl, aryl, alkoxy, aryloxy, alkylcarbonyl, alkylcarboxy, and arylthio. One suitable group of substituents is hydrogen, halogen, CN, OH, $NO_2$, amino, phenyl, $C_1$-$C_4$ alkoxy, phenoxy, $C_1$-$C_4$ alkylcarbonyl, $C_1$-$C_4$ alkylcarboxy and phenylthio.

The term "arylthio" as used herein refers to the S(aryl) group, where the point of attachment is through the sulfur-atom and the aryl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The term "alkoxy" as used herein refers to the O(alkyl) group, where the point of attachment is through the oxygen-atom and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The term "aryloxy" as used herein refers to the O(aryl) group, where the point of attachment is through the oxygen-atom and the aryl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylcarbonyl" as used herein refers to the C(O)(alkyl) group, where the point of attachment is through the carbon-atom of the carbonyl moiety and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylcarboxy" as used herein refers to the C(O)O(alkyl) group, where the point of attachment is through the carbon-atom of the carboxy moiety and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylamino" as used herein refers to both secondary and tertiary amines where the point of attachment is through the nitrogen-atom and the alkyl groups can be substituted, e.g., by 1 to 4 substituents, the same or different, selected from hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The alkyl groups can be the same or different.

The term "halogen" as used herein refers to Cl, Br, F, or I.

The term "aryl" as used herein refers to an aromatic, carbocyclic system, e.g., of 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents selected from halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, aryloxy, alkoxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl. Desirably, a substituted aryl group is substituted with 1 to 4 substituents which may be the same or different.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 tot 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of 6 to 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings. Suitable heterocyclic rings include those having 6 to 12, preferably 6 to 10 ring members containing 1 to 3 heteroatoms selected from N, O and S. Suitable heteroaryl rings include those having 5 to 12 preferably 5 to 10 ring members containing 1 to 3 heteroatoms selected from N, O and S.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to 4 heteroatoms in the backbone of the ring which may suitably be selected from O, S and N. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents, the same or different selected from halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, aryloxy, alkoxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl. A substituted heterocycle or heteroaryl group may have 1, 2, 3, or 4 substituents.

The compounds may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyl-dimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds discussed herein also encompass "metabolites" which are unique products formed by processing the compounds by the cell or subject. Desirably, metabolites are formed in vivo.

II. Methods of Preparing the Compounds

The compounds described herein are readily prepared by one of skill in the art according to the following schemes using commercially available starting materials or starting materials which can be prepared using literature procedures. These schemes show the preparation of representative compounds. Variations on these methods, or other methods known in the art, can be readily performed by one of skill in the art given the information provided herein.

As shown in Scheme 1, an appropriately substituted aryl or heteroaryl bromomethylketone 1 is reacted with potassium thiocyanate in a solvent such as ethanol to give the thiocyanate 2. Reaction of 2 with 30% HBr in acetic acid provides the 2-bromo-4-aryl or heteroaryl thiazole 3. For compounds whereby W is oxygen, 3 is heated with amine 4 to provide 5. Cyclization of 5 using a variety of activated reagents, including triphosgene and 1,1'-carbonyldiimidazole, gives 7. Additional activated reagents can be used to prepare 7 and are provided in the examples set forth below.

For compounds whereby W is $NR_{10}$, alcohol 8 is oxidized to give 9. Reaction of 9 with an amine, such as $NH_2R_{10}$, followed by a reduction provides 10. Cyclization of 10, using the cyclization described above for 7, provides compound 11.

For compounds whereby W is $CR_{11}R_{12}$ and V is O, carbonyl 9 is reacted with a phosphonate ester, such as $(CH_3O)_2P(O)CH_2CO_2CH_3$, using a base, such as sodium hydride, in a suitable solvent, such as tetrahydrofuran (THF), to give unsaturated ester 12. Reduction of 12 with a catalyst, such as 10% palladium on carbon in a suitable solvent, provides saturated ester 13. Cyclization of 13 under basic conditions, including using a base such as sodium bis(trimethylsilyl) amide in a solvent such as THF, provides saturated amide 14. Alternatively, 12 can be treated with a base such as sodium methoxide in a solvent such as THF to give unsaturated amide 14.

Scheme 1

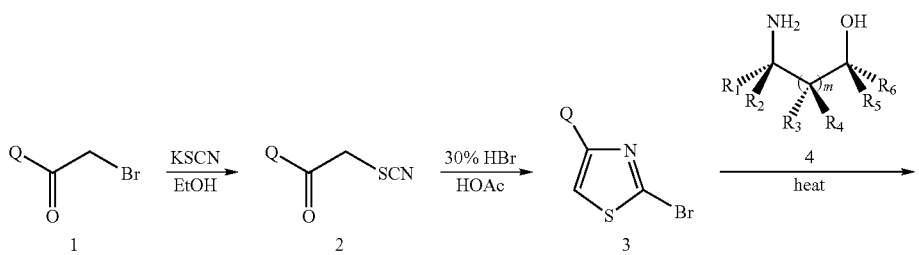

-continued
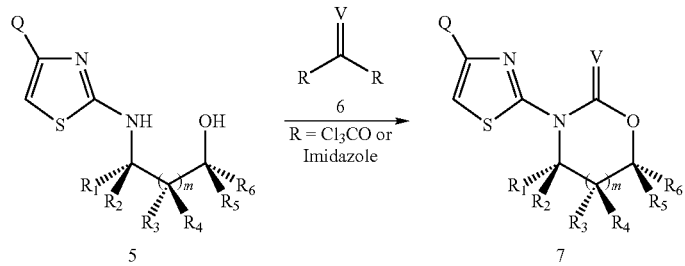
For W = O
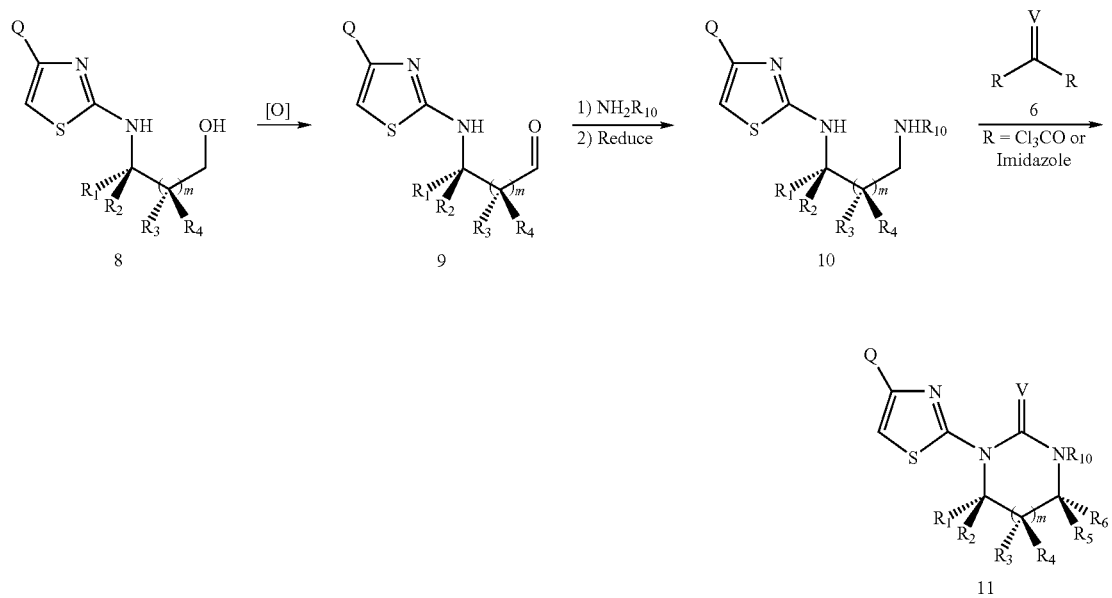
For W = NR_{10}
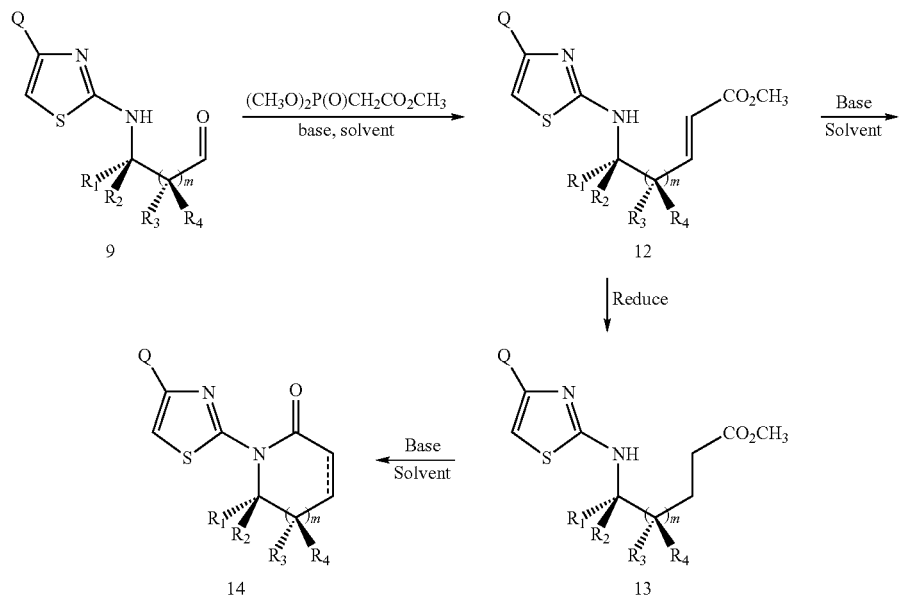

An alternate route to the thiazole derivatives is shown in Scheme 2. Reaction of amine 4 with benzoyl isothiocyanate 15 provides benzoyl thiourea 16, which is then hydrolyzed to thiourea 17. Reaction of 17 with the appropriately substituted aryl or heteroaryl bromomethylketone 1 provides thiazole 5, which is cyclized to 7 as previously described in Scheme 1.

A third route to the thiazole derivatives is shown in Scheme 3. Reaction of amino ester salt 18 with thiocyanate 2 using a base, such as triethylamine, and an appropriate solvent, such as ethanol, gives aminothiazole 19. Reduction of 19 with a reducing agent, such as lithium aluminum hydride, and subsequent cyclization as previously described in Scheme 1 provides thiazole 20.

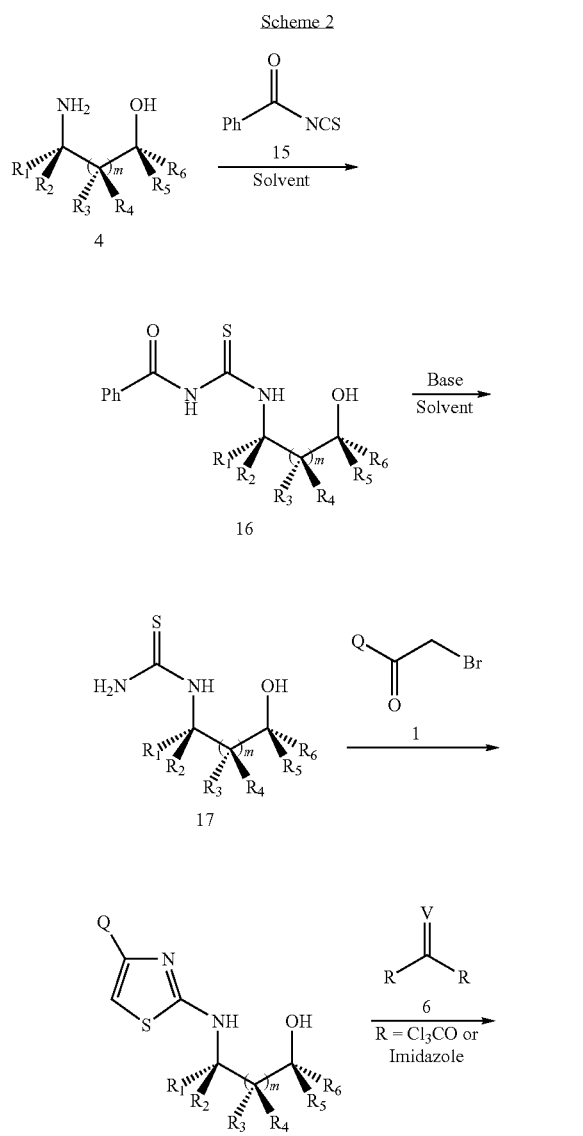

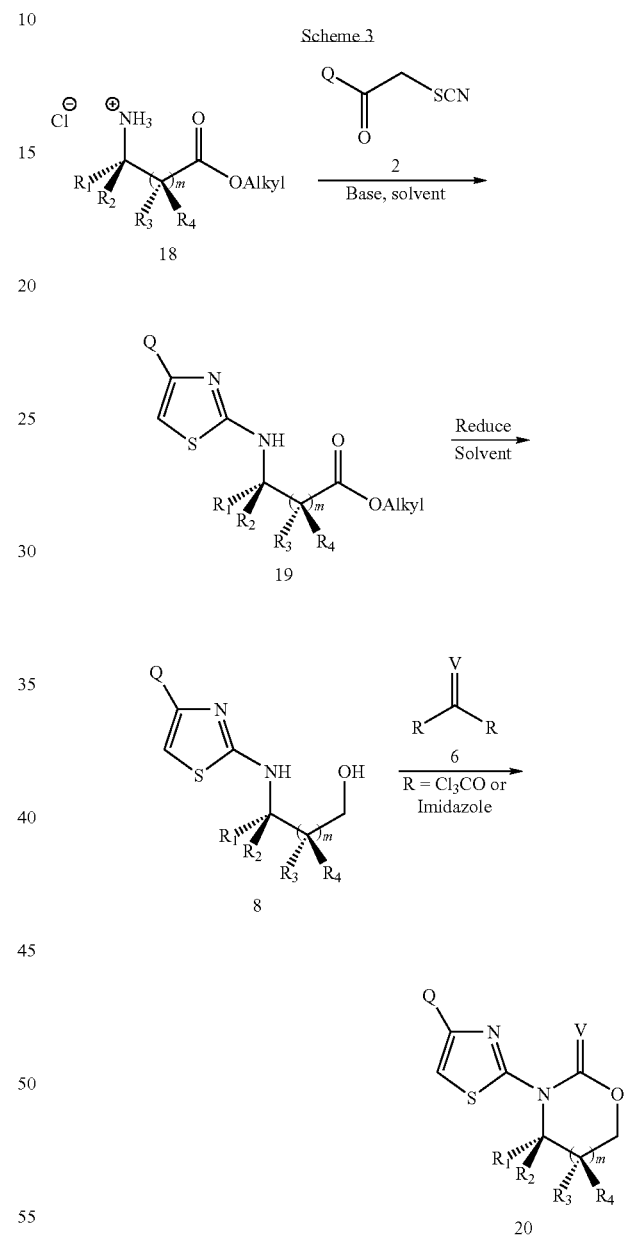

The introduction of either fluorine or chlorine at the five position of the thiazole ring is shown in Scheme 4. In the case of fluorine, reaction of cyclized thiazole 22 with an electrophilic fluorinating agent, such as the Selectfluor® reagent, directly provides fluoro derivative 25. However, in the case of the chlorine, aminothiazole 21 is first reacted with a positive source of chlorine, such as N-chlorosuccinimide, to give the five substituted thiazole 23, which is cyclized as previously described in Scheme 1 to give 24.

Scheme 4

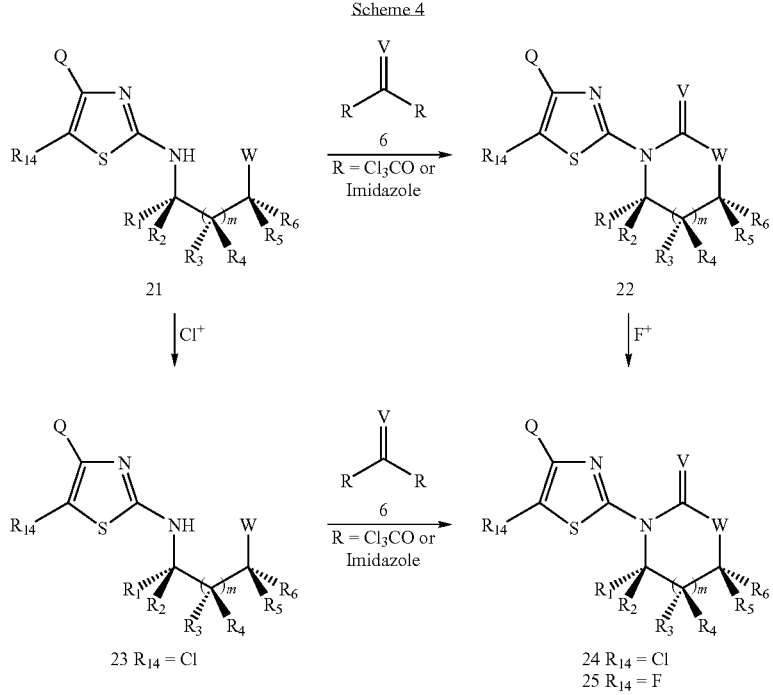

The preparation of derivatives having a trifluoromethyl group in the four position of the oxazolidinone ring is shown in Scheme 5. Reaction of 26 with the ethyl trifluoropyruvate 27 in the presence titanium (IV) chloride in a suitable solvent, such as methylene chloride, followed by reduction with a reducing agent, such as sodium cyanoborohydride, provides trifluoromethyl methyl ester 28. Further reduction of ester 28 to the alcohol 29, using, e.g, lithium aluminum hydride, followed by cyclization as previously described in Scheme 1, provides trifluoromethyl derivative 30.

Scheme 5

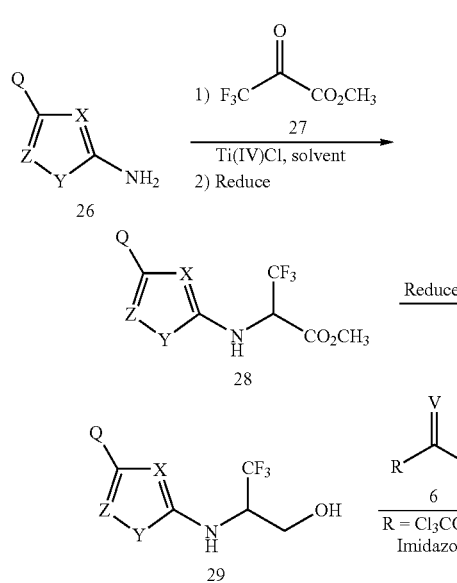

-continued

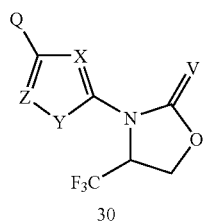

The preparation of oxazole derivatives is shown in Scheme 6. Heating an appropriately substituted aryl bromomethylketone 1 with an amide, such as formamide, provides oxazole 32. Reaction of 32 with a base, such as sodium bis(trimethylsilyl)amide in THF, followed by the addition of iodine, provides 2-iodooxazole 33. Reaction of 34 with sodium hydride, followed by the addition of 33, and heating at 170° C. for 2 hours gives oxazole 35.

Scheme 6

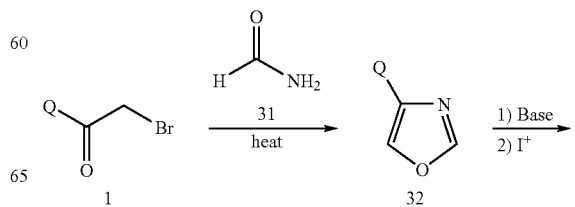

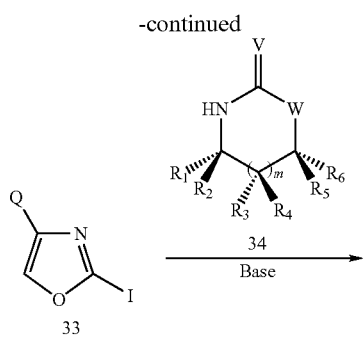

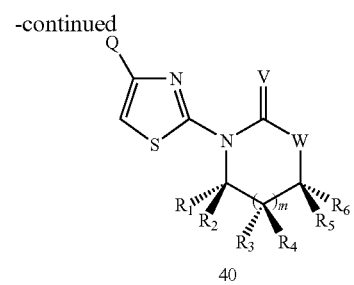

An alternative method for introducing the aryl group is shown in Scheme 8. Reaction of triflate 41 with the appropriately substituted arylboronic acid 42 in the presence of a catalyst, such as tetrakis(triphenylphosphine)palladium (0), in a solvent containing a base, gives 43.

Scheme 8

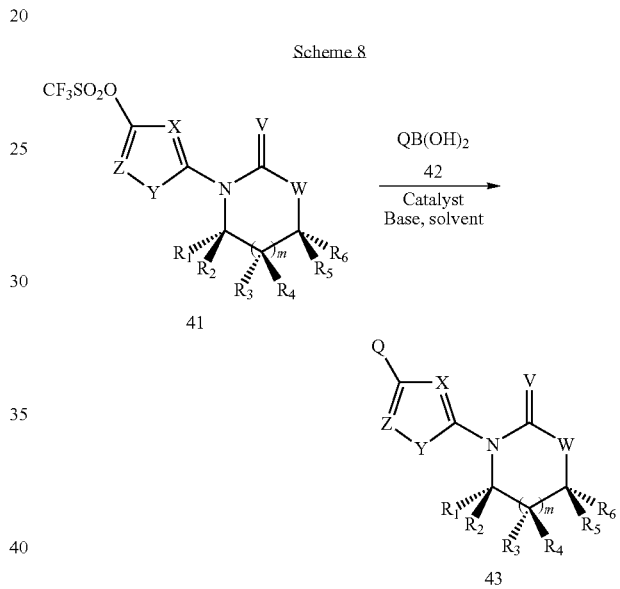

The preparation of thiadiazole derivatives is shown in Scheme 7. Reaction of an appropriately substituted amidine 36 with trichloromethanesulfenyl chloride in the presence of a base, such as triethylamine, and a suitable solvent, such as methylene chloride, gives 5-chloro substituted thiadiazole 37. Heating 37 with amine 38 at elevated temperatures of about 125° C. gives thiadiazole 39. The thiadiazole 39 is then cyclized to 40 as previously described in Scheme 1.

Scheme 7

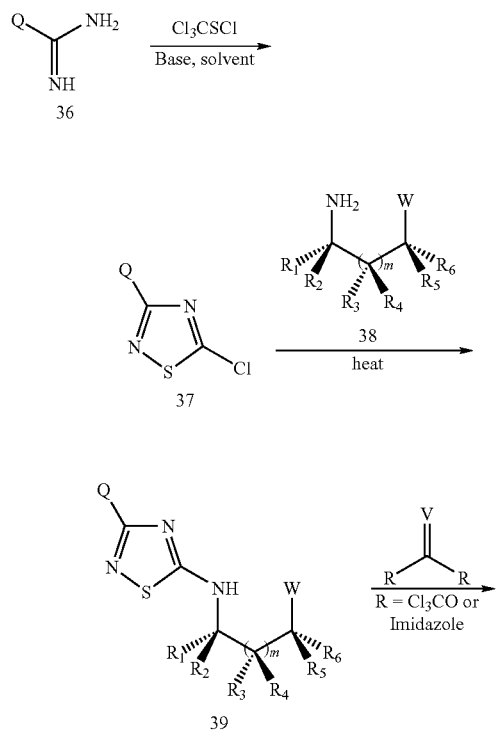

The preparation of thiophene derivatives is described in Scheme 9. Specifically, 2,4-dibromothiophene 44 is reacted with amine 34 in the presence of copper (I) iodide, in a solvent, such as dioxane, containing an amine base and cesium carbonate, at elevated temperature of about 110° C. provides the 2-substituted-4-bromothiophene 45. Reaction of 45 with the appropriately substituted arylboronic acid 42, in a similar manner as described in Scheme 8, gives thiophene 46.

Scheme 9

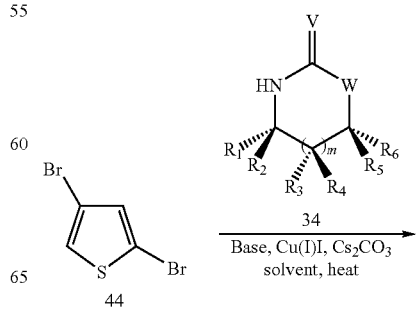

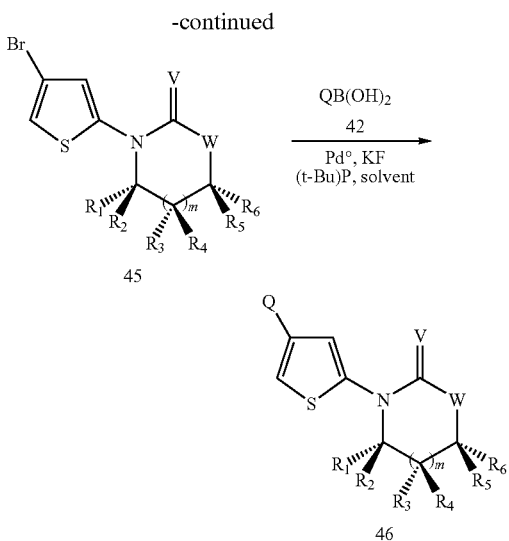

III. Methods of Using the Compounds

Also provided are pharmaceutical compositions containing one or more compounds described herein and a pharmaceutically acceptable carrier or excipient. In one embodiment, the methods of treatment include administering to a mammal a pharmaceutically effective amount of one or more compounds as described herein as progesterone receptor modulators.

The compounds may be combined with one or more pharmaceutically acceptable carriers or excipients, e.g., solvents, diluents and the like. Suitably, the compounds are formulated for delivery to a subject by any suitable route including, e.g., transdermal, mucosal (intranasal, buccal, vaginal), oral, parenteral, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the compounds may be combined with one or more of a solid carrier, liquid carrier, adjuvant, suspending agent, syrup, and elixir, among others, the selection of which is dependent on the nature of the active ingredient and the particular form of administration desired.

Solid carriers include, without limitation, starch, lactose, dicalcium phosphate, microcrystalline cellulose, sucrose and kaolin.

Liquid carriers include, without limitation, sterile water, dimethylsulfoxide (DMSO), polyethylene glycols, non-ionic surfactants and edible oils such as corn, peanut and sesame oils.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the compound may be combined with a suspending agent, including about 0.05 to about 5% of suspending agent.

In another embodiment, the compound may be combined with a syrup containing, e.g., about 10 to about 50% of sugar.

In a further embodiment, the compound may be combined with an elixir containing, e.g., about 20 to about 50% ethanol, and the like.

When formulated for oral delivery, the compounds can be in the form of a tablet, capsule, caplet, gel tab, dispersible powder, granule, or suspension. One particularly desirable pharmaceutical composition, from the standpoint of ease of preparation and administration, are solid compositions, particularly tablets and hard-filled or liquid-filled capsules.

The compounds may also be administered parenterally or intraperitoneally as solutions, suspensions, dispersions, or the like. Such pharmaceutical preparations may contain, e.g., about 25 to about 90% of the compound in combination with the carrier. Desirably, the pharmaceutical preparation contains about 5% and 60% by weight of the compound. In one embodiment, the compounds are administered in solutions or suspensions, whereby the compounds are present as free bases or pharmacologically acceptable salts and are prepared in water suitably mixed with a surfactant such as hydroxypropylcellulose. In another embodiment, the solutions or suspensions containing the compound may contain about 0.05 to about 5% of a suspending agent in an isotonic medium. In a further embodiment, the compounds are administered in dispersions, which may be prepared in glycerol, polyethylene glycols and mixtures thereof in oils.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to cycle to which the compound is being administered, including a 28-day cycle. However, the vaginal ring can be inserted for longer or shorter periods of time. See, U.S. Pat. Nos. 5,972,372; 6,126,958; and 6,125,850, which are hereby incorporated by reference, for formulations of the vaginal ring that can be used.

The compounds can also be delivered via a transdermal patch. Suitably, use of the patch is timed to the length of the cycle, including a 28 day cycle. However, the patch can remain in place for longer or shorter periods of time.

The compounds may be utilized in methods of contraception, hormone replacement therapy, and the treatment and/or prevention of benign and malignant neoplastic disease; cycle-related symptoms; fibroids, including uterine fibroids; leiomyoma; endometriosis; benign prostatic hypertrophy; carcinomas and adenocarcinomas of the endometrium, ovary, breast, colon, prostate, pituitary, meningioma and other hormone-dependent tumors; dysmenorrhea; dysfunctional uterine bleeding; symptoms of premenstrual syndrome and premenstrual dysphoric disorder; and for inducing amenorrhea. Additional uses of the present progesterone receptor modulators include the synchronization of estrus in livestock. In one embodiment, the neoplastic disease is hormone-dependent.

The term "cycle-related symptoms" refers to psychological symptoms (e.g., mood change, irritability, anxiety, lack of concentration, or decrease in sexual desire) and physical symptoms (e.g., dysmenorrhea, breast tenderness, bloating, fatigue, or food cravings) associated with a woman's menstrual cycle. Cycle-related symptoms include, but are not limited to, dysmenorrhea and moderate to severe cycle-related symptoms.

When utilized for these purposes, the compounds can be administered in combination with other agents, as well as in combination with each other. Such agents include, without limitation, progestins, antiprogestins, estrogens, antiestrogens, selective estrogen receptor modulators (SERMS), among others. Progestins can include, without limitation, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, (17-deacetyl)norgestimate. Estrogens can include, without limitation, ethinyl estradiol. The compounds described herein can be combined with one or more of these agents, delivered concurrently therewith one or more of these agents, delivered prior to one or more of these agents, or delivered subsequent to one or more of these agents.

A patient or subject being treated is a mammalian subject and typically a female. Desirably, the subject is a human. However, as used herein, a female can include non-human mammals, e.g., cattle or livestock, horses, pigs, domestic animals, etc.

The effective dosage of the compound may vary depending on the particular compound employed, the mode of administration and the severity of the condition being treated. However, in general, satisfactory results are obtained when the compounds are administered at a daily dosage of about 0.5 to about 500 mg/kg of animal body weight, about 1 to about 400 mg/kg, about 5 to about 300 mg/kg, about 10 to about 250 mg/kg, about 50 to about 200 mg/kg, or about 100 to 150 mg/kg. For most large mammals, the total daily dosage is from about 1 to 100 mg. In one embodiment, the total daily dosage is from about 2 to 80 mg. This dosage regimen may be adjusted to provide the optimal therapeutic response. For example, several divided doses may be administered daily or the dose may be proportionally reduced as indicated by the exigencies of the therapeutic situation.

As previously noted, the compounds may be administered via a vaginal ring. In one embodiment, the ring is inserted into the vagina and it remains in place for 3 weeks. During the fourth week, the vaginal ring is removed and menses occurs. The following week, a new ring is inserted to be worn another 3 weeks until it is time for the next period. In another embodiment, the vaginal ring is inserted weekly and is replaced for 3 consecutive weeks. Then, following 1 week without the ring, a new ring is inserted to begin a new regimen. In yet another embodiment, the vaginal ring is inserted for longer or shorter periods of time.

Further, the previously mentioned transdermal patch is applied via a suitable adhesive on the skin, where it remains in place for at least one week. In one embodiment, the transdermal patch remains in place for one week and is replaced weekly for a total of 3 weeks. In another embodiment, the transdermal patch remains in place for two weeks. In a further embodiment, the transdermal patch remains in place for three weeks. During the fourth week, no patch is applied and menses occurs. The following week, a new patch is applied to be worn to begin a new regimen. In yet another embodiment, the patch remains in place for longer or shorter periods of time.

When used for contraception, the method typically includes delivering a daily dosage unit containing a compound for 28 consecutive days to a female of child-bearing age. Desirably, the method includes delivering the compound over a period of 21 to 27 consecutive days followed by 1 to 7 consecutive days in which no effective amount or no amount of the compound is delivered. Optionally, the period of 1 to 7 days in which no effective amount of the compound is delivered to the subject can involve delivery of a second phase of daily dosage units of 1 to 7 days of a pharmaceutically acceptable placebo. Alternatively, during this "placebo period", no placebo is administered. The compound may optionally be administered in combination with a progestin, antiprogestin, estrogen, or combination thereof.

In another embodiment, the method includes delivering a compound for 21 consecutive days, followed by 7 days in which no effective amount of the compound is delivered. Optionally, during these 7 days, a second phase of 7 daily dosage units of an orally and pharmaceutically acceptable placebo can be delivered. The compound may optionally be administered in combination with a progestin, antiprogestin, estrogen, anti-estrogen, SERM or combination thereof.

In a further embodiment, the method includes delivering a compound for 23 consecutive days, followed by 5 days in which no effective amount of the compound is delivered. Optionally, during these 5 days, a second phase of 5 daily dosage units of an orally and pharmaceutically acceptable placebo can be delivered. The compound may optionally be administered in combination with a progestin, antiprogestin, estrogen, anti-estrogen, SERM or combination thereof.

In yet another embodiment, the method includes delivering a compound for 25 consecutive days, followed by 3 days in which no effective amount of the compound is delivered. Optionally, during these 3 days, a second phase of 3 daily dosage units of an orally and pharmaceutically acceptable placebo can be delivered. The compound may optionally be administered in combination with a progestin, antiprogestin, estrogen, anti-estrogen, SERM, or combination thereof.

In still a further embodiment, the method includes delivering a compound for 27 consecutive days, followed by 1 day in which no effective amount of the compound is delivered. Optionally, a second phase of 1 daily dosage unit of an orally and pharmaceutically acceptable placebo can be delivered. The compound may optionally be administered in combination with a progestin, antiprogestin, estrogen, anti-estrogen, SERM, or combination thereof.

In another embodiment, a method of contraception includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet a further embodiment, a method of contraception includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

In yet a further embodiment, a method of contraception is provided and includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In another embodiment, a method of contraception is provided and includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

Also provided are kits or packages of pharmaceutical formulations designed for use in the regimens described herein. Suitably, the kits contain one or more compounds as described herein.

Advantageously, for use in the kits, the compound is formulated for the desired delivery vehicle and route. For example, the compound can be formulated for oral delivery, parenteral delivery, vaginal ring, transdermal delivery, or mucosal delivery, as discussed in detail above. The kit is preferably a pack (e.g. a blister pack) containing daily doses arranged in the order in which they are to be taken.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional phases, including any second and third phases. To help facilitate compliance with each regimen, it is also preferred that the kits contain the placebo described for the final days of the cycle. It is further preferred that each package or kit contain a pharmaceutically acceptable package having indicators for each day of the 28-day cycle, such as a labeled blister package, dial dispenser, or other packages known in the art.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

In one embodiment, the kit is designed for daily oral administration over a 28-day cycle, desirably for one oral administration per day, and organized so as to indicate a single oral formulation or combination of oral formulations to be taken on each day of the 28-day cycle. Desirably each kit will include oral tablets to be taken on each the days specified; desirably one oral tablet will contain each of the combined daily dosages indicated. For example, a kit can contain 21 to 27 daily dosage units of an effective amount of the compound, optionally, 1 to 7 daily dosage units of a placebo and other appropriate components including, e.g., instructions for use.

In another embodiment, the kit is designed for weekly or monthly administration via a vaginal ring over a 28-day cycle. Suitably, such a kit contains individual packaging for each of the vaginal rings, i.e. one to three, required for a monthly cycle and other appropriate components, including, e.g., instructions for use.

In a further embodiment, the kit is designed for weekly or monthly administration via a transdermal patch over a 28-day cycle. Suitably, such a kit contains individual packaging for each of the patches, i.e. one to three, required for a monthly cycle and other appropriate components including, e.g., instructions for use.

In still another embodiment, the kit is designed for parenteral delivery of the compound. Such a kit is typically designed for delivery at home and may include needles, syringes, and other appropriate packaging and instructions for use.

In yet another embodiment, the kit contains the compound in a gel or cream formulation. Optionally, the kit can include appropriate packaging such as a tube or other container, an applicator, and/or instructions for use.

In a further embodiment, the kit includes (a) a first phase of from 14 to 21 daily dosage units of a progestational agent equal in progestational activity to about 35 to about 150 µg levonorgestrel; (b) a second phase of from 1 to 11 daily dosage units of a compound described herein; and (c) a third phase of daily dosage units of an orally and pharmaceutically acceptable placebo; wherein the total number of the daily dosage units in the first phase, second phase and third phase equals 28.

In still another embodiment, a kit contains (a) a first phase of from 14 to 21 daily dosage units of a compound described herein; (b) a second phase of from 1 to 11 daily dosage units of an antiprogestin compound; and (c) a third phase of daily dosage units of an orally and pharmaceutically acceptable placebo; wherein the total number of the daily dosage units in the first phase, second phase and third phase equals 28.

The following examples are illustrative only and are not intended to be a limitation on the present invention.

EXAMPLES

Example 1

(4R)-3-[4-(4-Bromophenyl)-1,3-thiazol-2-yl]-4-methyl-1,3-oxazolidin-2-one

Step 1: 2-(4-Bromophenyl)-2-oxoethyl thiocyanate

A mixture of 2,4'-dibromoacetophenone (56.08 g, 0.20 mol) and potassium thiocyanate (21.57 g, 0.22 mol) in 1 L of absolute ethanol was stirred under nitrogen at room temperature for 5 h. The reaction was added to 2 L of water and the mixture stirred at room temperature for 2 h. The solid present was collected by filtration, rinsed with water, ice-cold ethanol, hexane, and then dried under high vacuum to give 2-(4-bromophenyl)-2-oxoethyl thiocyanate (50.39 g, 98%) as a white solid, mp 148-149° C.

Step 2: 2-Bromo-4-(4-bromophenyl)-1,3-thiazole

A suspension of 2-(4-bromophenyl)-2-oxoethyl thiocyanate (5.12 g, 20.0 mmol), prepared in the previous step, in 30 mL of 30% hydrogen bromide in acetic acid was stirred under nitrogen at room temperature for 7 h. The yellow suspension was poured into 200 mL of 1 N NaOH (exotherm) and the mixture stirred at room temperature for 17 h. The solid present was collected by filtration, rinsed with water, ice-cold ethanol, hexane and then dried under high vacuum to give 2-bromo-4-(4-bromophenyl)-1,3-thiazole (5.36 g, 84%) as a light yellow solid, mp 117-119° C.; MS (ES) m/z 318/320/322 [M+H]$^+$.

Step 3: (2R)-2-{[4-(4-Bromophenyl)-1,3-thiazol-2-yl]amino}propan-1-ol

A mixture of 2-bromo-4-(4-bromophenyl)-1,3-thiazole (3.00 g, 9.41 mmol), prepared in the previous step, and (R)-(−)-2-amino-1-propanol (2.20 mL, 28.3 mmol) was stirred under nitrogen at 150° C. for 11.5 h. The reaction was dissolved in 20% methanol-methylene chloride and extracted with 5% NaHCO$_3$. The organic layer was separated and the aqueous layer was extracted three times with 20% methanol-methylene chloride. The combined extracts were dried (anhydrous MgSO$_4$), filtered and the solvent removed under reduced pressure to give 3.08 g of a yellow residue. Purification of the residue on 500 g of silica gel (230-400 mesh) using 1:1 methylene chloride-hexane to methylene chloride as the eluents to remove starting material and non-polar impurities and then 30% ethyl acetate-methylene chloride gave (2R)-2-{[4-(4-bromophenyl)-1,3-thiazol-2-yl]amino}propan-1-ol (2.09 g, 71%) as a yellow oil, MS (ES) m/z 313.0 [M+H]$^+$.

Step 4: (4R)-3-[4-(4-Bromophenyl)-1,3-thiazol-2-yl]-4-methyl-1,3-oxazolidin-2-one Triphosgene (2.62 g, 8.82 mmol) in 60 mL of methylene chloride was added under nitrogen dropwise over 1.75 h to a solution of (2R)-2-{[4-(4-bromophenyl)-1,3-thiazol-2-yl]amino}propan-1-ol (2.30 g, 7.33 mmol), prepared in the previous step, and N,N-diisopropylethylamine in 125 mL of methylene chloride at ice-bath temperature. After the addition the reaction was stirred at ice-bath temperature for 3.5 h. The ice bath was removed and the stirring continued for 15 h. The reaction was extracted with 2 N HCl, dried (anhydrous MgSO$_4$), filtered and the solvent removed under reduced pressure to give 2.81 g of a yellow solid. Purification on the solid on 500 g of silica gel (230-400 mesh) using 30% methylene chloride-hexane to methylene chloride as the eluents gave the title compound (2.07 g, 83%) as a white solid, mp 197-199° C.; MS (ES) m/z 339.0 [M+H]$^+$; Anal. Calcd for $C_{13}H_{11}BrN_2O_2S$: C, 46.03; H, 3.27; N, 8.26. Found: C, 45.80; H, 3.13; N, 8.16.

Example 2

(4R)-3-[4-(4-Bromophenyl)-1,3-thiazol-2-yl]-4-propyl-1,3-oxazolidin-2-one

Step 1: (2R)-2-{[4-(4-Bromophenyl)-1,3-thiazol-2-yl]amino}pentan-1-ol

A mixture of 2-bromo-4-(4-bromophenyl)-1,3-thiazole (2.9 g, 9.09 mmol), prepared in step 2 of Example 1, and (R)-(−)-2-amino-pentanol (2.82 g, 27.2 mmol) was stirred under nitrogen at 150° C. for 18 h. After cooling to room temperature, the residue was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% ethyl acetate-hexane to 100% ethyl acetate gave (2R)-2-{[4-(4-bromophenyl)-1,3-thiazol-2-yl]amino}pentan-1-ol (2.56 g, 83%) as a yellow solid, mp 63-65° C.; MS (ESI) m/z 341 [M+H]$^+$.

Step 2: (4R)-3-[4-(4-Bromophenyl)-1,3-thiazol-2-yl]-4-propyl-1,3-oxazolidin-2-one In the same manner as described in step 4 of Example 1, and replacing (2R)-2-{[4-(4-bromophenyl)-1,3-thiazol-2-yl]amino}propan-1-ol with (2R)-2-{[4-(4-bromophenyl)-1,3-thiazol-2-yl]amino}pentan-1-ol (2.4688 g, 7.23 mmol), prepared in the previous step, gave a brown residue. The residue was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% ethyl acetate-hexane to 100% ethyl acetate gave the title compound (2.172 g, 84%) as a white solid, mp 114-116° C.; MS (ESI) m/z 367 [M+H]$^+$. Anal. Calcd for $C_{15}H_{15}BrN_2O_2S$: C, 49.06; H, 4.12; N, 7.63. Found: C, 49.13; H, 3.91; N, 7.57.

Examples 3 and 4 were prepared in a similar manner as described in Example 1. In step 3 of Example 1 (R)-(−)-2-amino-1-propanol is replaced with the appropriate amine. After heating at 150° C. for the required period of time the crude reaction product can be purified in a manner similar to that described in either step 3 of Example 1 or step 1 of Example 2. The purified products are then treated with triphosgene in the same manner as described in step 4 of Example 1. The crude products can be purified in a manner similar to that described in either step 4 of Example 1 or step 2 of Example 2.

Example 3

3-[4-(4-Bromophenyl)-1,3-thiazol-2-yl]-1,3-oxazinan-2-one mp 225-227° C.; MS (ESI) m/z 339 [M+H]$^+$.

Example 4

3-[4-(4-Bromophenyl)-1,3-thiazol-2-yl]-5,5-dimethyl-1,3-oxazinan-2-one mp 169-171° C.; MS (ESI) m/z 367 [M+H]$^+$.

Example 5

(1) Effects of Progestins and Antiprogestins on Alkaline Phosphatase Activity in T47D Cells PURPOSE: To identify progestins or antiprogestins by determining a compound's effect on alkaline phosphatase activity in T47D cells.

A. Reagents:
 Culture Medium:
  DMEM:F12 (1:1) (GIBCO, BRL) supplemented with 5% (v/v) charcoal stripped fetal bovine serum (not heat-inactivated), 100 U/mL penicillin, 100 μg/mL streptomycin, and 2 mM the GlutaMax™ reagent (GEBCO, BRL).
 Alkaline phosphatase assay buffer:
  I. 0.1M Tris-HCl, pH 9.8, containing 0.2% the Triton® X-100 reagent
  II. 0.1M Tris-HCl, pH 9.8, containing 4 mM p-nitrophenyl phosphate (Sigma).

B. Cell Culture and Treatment:
 Frozen T47D cells were thawed in a 37° C. water bath and diluted to 280,000 cells/mL in culture medium. To each well in a 96-well plate (Falcon, Becton Dickinson Labware), 180 μL of diluted cell suspension was added.

Twenty μL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 h. NOTE: For high throughput screening, one concentration of each compound was tested at 0.3 µg/mL. Based on an average molecular weight of 300 g/mol for the compounds in the library, the concentration was approximately 1 µM. Subsequently, active compounds were tested in dose response assays to determine $EC_{50}$ and $IC_{50}$.

C. Alkaline Phosphatase Enzyme Assay:

At the end of treatment, the medium was removed from the plate. Fifty µL of assay buffer I was added to each well. The plates were shaken in a titer plate shaker for 15 min. Then 150 µL of assay buffer II was added to each well. Optical density measurements were taken at 5 min intervals for 30 min at a test wavelength of 405 nM.

D. Analysis of Results:

For reference and test compounds, a dose response curve was generated for dose (X-axis) vs. the rate of enzyme reaction (slope) (Y-axis). Square root-transformed data was used for analysis of variance and nonlinear dose response curve fitting for both agonist and antagonist modes. Huber weighting was used to down-weight the effects of outliers. $EC_{50}$ or $IC_{50}$ values were calculated from the retransformed values. JMP software (SAS Institute, Inc.) was used for both one-way analysis of variance and non-linear dose response analysis in both single dose and dose response studies.

E. Reference Compounds:

Progesterone and trimegestone were reference progestins and RU486 was the reference antiprogestin. All reference compounds were run in full dose response curves and the $EC_{50}$ and $IC_{50}$ values were calculated.

(2) Progesterone Receptor Whole Cell Competition Binding Assay Using T47D Cells.

PURPOSE: To evaluate the progesterone receptor (PR) binding activity of progestins or antiprogestins in live, intact (whole) cells using the human breast carcinoma T47D cell line and $^3$H-progesterone as the labeled ligand.

A. Reagents:
 Culture Medium:
  5% RC: phenol red free DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM the GlutaMax™ reagent (GIBCO, BRL).
  10% RC: Same as above supplemented with 10% (v/v) FBS.
 $^3$H-Progesterone: Perkin Elmer Life Science, cat# NET-381 (typically around 102 Ci/mmol)
 Liquid Scintillation Cocktail:
  the Ready-Safe™ cocktail, cat# 141349 (Beckman Coulter)
 Tissue Culture Plates:
  96 well, clear bottom, white, plates: VWR Part #: 29443-150 or Perkin Elmer Part #: 3983498

B: T47D Cell Culture:

T47D cells were maintained in 10% RC media at 37° C. in a 5% $CO_2$/humidified atmosphere and were split twice weekly for proper response. Cells were plated in 10% RC the day before binding assay at 50,000 cells per well in the white, clear bottom plates purchased through VWR or Perkin Elmer.

C: Binding Assay:

Cells plated the day prior to the assay in white clear bottom plates were used. A master compound plate was set up containing control and test compounds at 20× final desired concentration for the competition binding. A typical dose range of 20× concentrations were (in nM); 200,000; 20,000; 6000; 2000; 600; 200; 20; and 2. Final concentrations were (in nM); 10,000; 1000; 300; 100; 30; 10; 1; 0.1. Control compounds were typically run 10-fold lower than this and include a 0, or vehicle, control well. A stock of 60 nM $^3$H-progesterone (20×) were also prepared at a volume needed of 10 µL per well.

Media on cells were replaced with 180 µL of 5% RC. Ten microliters (10 µL) of 60 nM $^3$H-progesterone (for final concentration of 3 nM) was added immediately, followed by 10 µL of 20× test or control compounds. Compounds were incubated for 3 h at 37° C. (A time course study found no difference between 2 and 4 h incubation.)

Following incubation, media was carefully removed and cells were washed 3× with 200 µL 5% RC each wash. Fifty microliters of liquid scintillation cocktail was added and the plates were shaken vigorously for a minimum of 15 min. Plates were read on the Wallac Microbeta® 1450 plate reader.

D. Analysis of Results:

Square root-transformed data were used for analysis of variance and calculation of $IC_{50}$. SAS software (SAS Institute, Inc.) was used for all the statistical analysis.

E. Reference Compounds:

Progesterone was used as a reference progestin and RU486 as a reference antiprogestin.

TABLE 1

| Example | T47D Alkaline Phosphatase Activity $IC_{50}$ (nM) or % inhibition |
|---|---|
| 3 | 237.6 |
| 4 | 1367 |

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure:

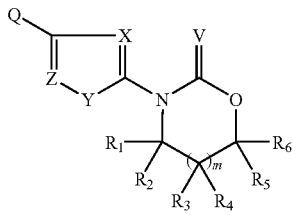

wherein:
 $R_1$, $R_2$, $R_3$, $R_4$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_nC(H)_{3-p}(R_7)_p$, —$(CH_2)_nCOOR_8$, or —$(CH_2)_p$—O—$R_9$; or
 $R_1$, $R_2$ or $R_3$, $R_4$ or $R_5$, $R_6$ are taken together to form a 3 to 6 membered cycloalkyl ring; or
 $R_1$ or $R_2$ forms a 5 to 7 membered cycloalkyl ring with $R_5$ or $R_6$; or
 $R_1$ or $R_2$ forms a carbocyclic 6-membered aromatic ring with $R_5$ or $R_6$;

$R_7$ is halogen;

$R_8$ is $C_1$ to $C_6$ alkyl;

$R_9$ is H, $C_1$ to $C_6$ alkyl, or $C_1$ to $C_3$ perfluoroalkyl;

V is O or S;

X and Z are, independently, N or $CR_{14}$;

$R_{14}$ is H, $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN;

Y is O or S;

Q is aryl, substituted aryl, heteroaryl, or substituted heteroaryl;

m is 1;

n is 0 to 3; and p is 1 to 3;

or a pharmaceutically acceptable salt or tautomer thereof.

2. The compound according to claim 1, wherein:

X is N;

Y is S;

Z is $CR_{14}$.

3. The compound according to claim 1, wherein:

X and Z are N;

Y is S.

4. The compound according to claim 1, wherein:

X is N;

Y is O;

Z is $CR_{14}$.

5. The compound according to claim 1, wherein V is O.

6. The compound of according to claim 1, wherein:

$R_1$ and $R_2$ are $C_1$ to $C_{10}$ alkyl;

$R_5$ and $R_6$ are H.

7. The compound according to claim 1, wherein Q is an aromatic ring.

8. The compound according to claim 7, wherein Q is an optionally substituted phenyl ring.

9. The compound according to claim 8, wherein said phenyl ring is substituted by one or more of $R_{15}$ and $R_{15}$ is $(CH_2)_n CN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl.

10. The compound according to claim 9, wherein $R_{15}$ is CN, halogen, or $NO_2$.

11. The compound according to claim 1, wherein Q is a heteroaryl ring substituted by one or more $R_{15}$, wherein $R_{15}$ is $(CH_2)_n CN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl.

12. The compound according to claim 1 of the structure:

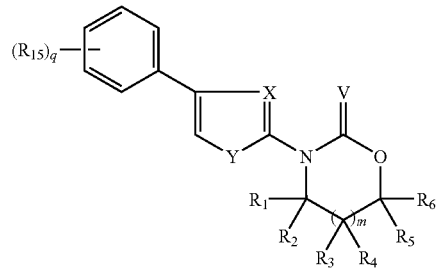

wherein:

$R_{15}$ is $(CH_2)_n CN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl; and q is 1 to 4.

13. The compound according to claim 1 of the structure:

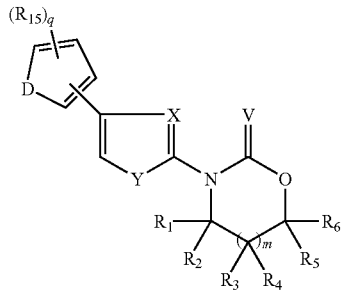

wherein:

D is S, $NR_{16}$, or O;

$R_{15}$ is $(CH_2)_n CN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl;

$R_{16}$ is H, $C_1$ to $C_6$ alkyl, $C_1$ to $C_6$ substituted alkyl, or —COO—($C_1$ to $C_6$ alkyl); and q is 1 to 3.

14. The compound according to claim 1 of the structure:

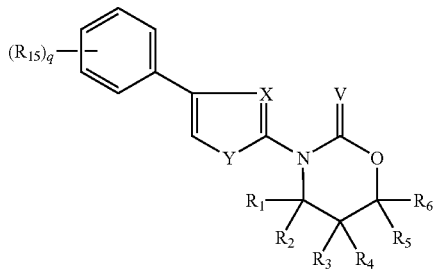

wherein:

$R_{15}$ is $(CH_2)_nCN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —$CO$—($C_1$ to $C_4$ alkyl), —$CO$—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl; and q is 1 to 4.

15. The compound according to claim 1 of the structure:

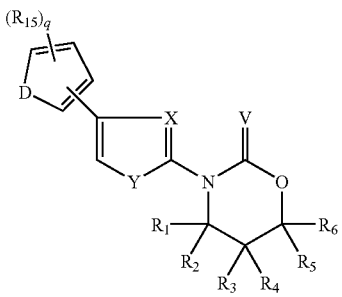

wherein:

D is S, $NR_{16}$, or O;

$R_{15}$ is $(CH_2)_nCN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$O(C_1$ to $C_4$ substituted alkyl), —$SO_2$—($C_1$ to $C_4$ alkyl), —$SO_2$—($C_1$ to $C_4$ substituted alkyl), —$CO$—($C_1$ to $C_4$ alkyl), —$CO$—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl;

$R_{16}$ is H, $C_1$ to $C_6$ alkyl, $C_1$ to $C_6$ substituted alkyl, or —COO—($C_1$ to $C_6$ alkyl); and q is 1 to 3.

16. The compound according to claim 1, wherein $R_1$, $R_2$, $R_5$, and $R_6$ are, independently, H or $C_1$ to $C_{10}$ alkyl.

17. The compound according to claim 1 which is selected from the group consisting of 3-[4-(4-Bromophenyl)-1,3-thiazol-2-yl]-1,3-oxazinan-2-one and 3-[4-(4-Bromophenyl)-1,3-thiazol-2-yl]-5,5-dimethyl-1,3-oxazinan-2-one.

18. A compound of the structure:

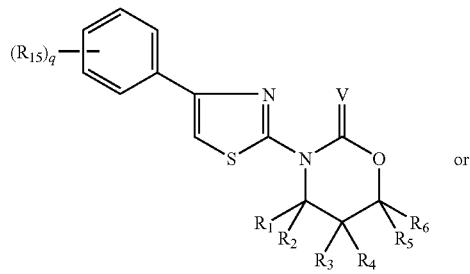

or

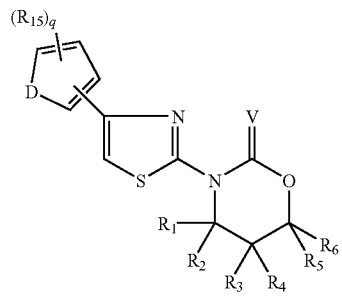

wherein:

$R_1$, $R_2$, $R_3$, $R_4$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_nC(H)_{3-p}(R_7)_p$, —$(CH_2)_nCOOR_8$, or —$(CH_2)_p$—O—$R_9$; or $R_1$, $R_2$, or $R_3$, $R_4$, or $R_5$, $R_6$ are taken together to form a 3 to 6 membered cycloalkyl ring;

$R_7$ is halogen;

$R_8$ is $C_1$ to $C_6$ alkyl;

$R_9$ is H, $C_1$ to $C_6$ alkyl, or $C_1$ to $C_3$ perfluoroalkyl;

D is S, $NR_{16}$, or O;

$R_{15}$ is $(CH_2)_nCN$, halogen, $NO_2$, —$C(NH_2)$=NOH, $C_1$ to $C_3$ perfluoroalkyl, $C_1$ to $C_3$ perfluoroalkoxy, —$O(C_1$ to $C_4$ alkyl), —$SO_2$—($C_1$ to $C_4$ alkyl), —$CO$—($C_1$ to $C_4$ alkyl), $C_1$ to $C_4$ alkyl, —O—$(CH_2)_n$-aryl, —COO—($C_1$ to $C_4$ alkyl), —CONH—($C_1$ to $C_3$ alkyl), —CON—($C_1$ to $C_3$ alkyl)$_2$, aryl, or heteroaryl;

$R_{16}$ is H, $C_1$ to $C_6$ alkyl, $C_1$ to $C_6$ substituted alkyl, or —COO—($C_1$ to $C_6$ alkyl);

V is O or S;

n is 0 to 3;

p is 1 to 3;

q is 1 to 3;

or a pharmaceutically acceptable salt, tautomer, metabolite, or prodrug thereof.

19. A compound of the structure:

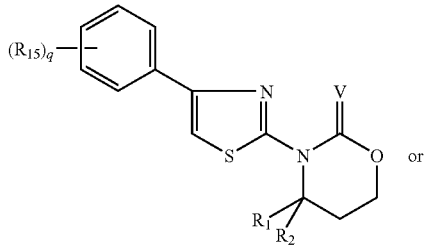

or

-continued

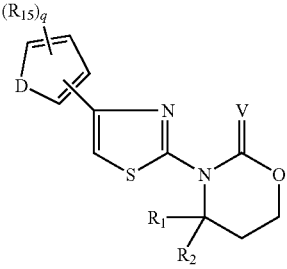

wherein:

R₁ and R₂ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n$COOR$_8$, or —$(CH_2)_p$—O—R$_9$; or R₁ and R₂ are taken together to form a 3 to 6 membered cycloalkyl ring;

R₇ is halogen;

R₈ is $C_1$ to $C_6$ alkyl;

R₉ is H, $C_1$ to $C_6$ alkyl, or $C_1$ to $C_3$ perfluoroalkyl;

D is S, NR$_{16}$, or O;

R₁₅ is $(CH_2)_n$CN, halogen, NO$_2$, —C(NH$_2$)=NOH, $C_1$ to $C_3$ perfluoroalkyl, $C_1$ to $C_3$ perfluoroalkoxy, —O($C_1$ to $C_4$ alkyl), —SO$_2$—($C_1$ to $C_4$ alkyl), —CO—($C_1$ to $C_4$ alkyl), $C_1$ to $C_4$ alkyl, —O—$(CH_2)_n$-aryl, —COO—($C_1$ to $C_4$ alkyl), —CONH—($C_1$ to $C_3$ alkyl), —CON—($C_1$ to $C_3$ alkyl)$_2$, aryl, or heteroaryl;

R₁₆ is H, $C_1$ to $C_6$ alkyl, $C_1$ to $C_6$ substituted alkyl, or —COO—($C_1$ to $C_6$ alkyl);

V is O or S;

n is 0 to 3;

p is 1 to 3;

q is 1 to 3;

or a pharmaceutically acceptable salt, tautomer, metabolite, or prodrug thereof.

20. A pharmaceutical composition comprising a compound of claim 1 and a pharmaceutically acceptable carrier.

21. A method of contraception comprising administering to a female in need thereof a compound of claim 1.

22. A method of treating uterine leiomyomata, endometriosis, dysfunctional bleeding, or polycystic ovary syndrome comprising administering to a female in need thereof a compound of claim 1.

\* \* \* \* \*